United States Patent
Yamaguchi et al.

(10) Patent No.: US 7,155,272 B2
(45) Date of Patent: Dec. 26, 2006

(54) CATHETER

(75) Inventors: Tetsu Yamaguchi, Tokyo (JP);
Hiroyuki Yagami, Fujinomiya (JP);
Yasukazu Harada, Fujinomiya (JP)

(73) Assignees: Terumo Kabushiki Kaisha, Tokyo
(JP); Tetsu Yamaguchi, Tokyo (JP)

( * ) Notice: Subject to any disclaimer, the term of this patent is extended or adjusted under 35 U.S.C. 154(b) by 278 days.

(21) Appl. No.: 10/654,940

(22) Filed: Sep. 5, 2003

(65) Prior Publication Data

US 2005/0101870 A1 May 12, 2005

(30) Foreign Application Priority Data

Sep. 5, 2002 (JP) .............................. 2002-260193

(51) Int. Cl.
*A61B 5/05* (2006.01)
*A61B 8/12* (2006.01)

(52) U.S. Cl. ...................... 600/425; 600/463; 600/467
(58) Field of Classification Search ................ 600/425, 600/439, 462–467; 604/103.04, 510
See application file for complete search history.

(56) References Cited

U.S. PATENT DOCUMENTS

| 5,024,234 A | | 6/1991 | Leary et al. | |
| 5,201,316 A | * | 4/1993 | Pomeranz et al. | 600/463 |
| 5,312,427 A | * | 5/1994 | Shturman | 606/159 |
| 5,327,885 A | * | 7/1994 | Griffith | 600/470 |
| 5,468,225 A | * | 11/1995 | Teirstein | 604/103.04 |
| 5,715,825 A | | 2/1998 | Crowley | |
| 5,976,093 A | * | 11/1999 | Jang | 600/462 |

\* cited by examiner

*Primary Examiner*—Francis J. Jaworski
(74) *Attorney, Agent, or Firm*—Buchanan Ingersoll & Rooney PC (57) ABSTRACT

An ultrasound catheter includes a transducer unit used for observation of the inside of an organism, observation lumens in which the transducer unit is disposed and which extend in the direction of insertion into the organism, a first guide wire lumen provided substantially in parallel to the observation lumens and on the distal end side in the insertion direction in relation to the transducer unit and through which a guide wire preliminarily brought to the inside of the organism is passed, and a second guide wire lumen provided on an extension line of the first guide wire lumen and on the proximal end side in the insertion direction in relation to the transducer unit and through which the guide wire is passed.

10 Claims, 6 Drawing Sheets

CATHETER

BACKGROUND OF THE INVENTION

The present invention relates to a diagnostic catheter used for various kinds of diagnosis by being inserted, into a body cavity or lumen such as a blood vessel, a vas, a digestive organ, etc., and particularly to a catheter used for display of a cross-sectional image of a lumen or the like purposes.

In a treatment of an anglostenosis portion possibly causing myocardial infarction or the like, an operative technique of treating the diseased part percutaneously by use of a catheter is used. The operative technique includes various methods such as a method of dilating the angiostenosis portion by a dilation catheter having a balloon at its distal end, a method of causing a metallic pipe called stent to indwell in the angiostenosis portion, a method of excising the angiostenosis portion through rotation of a grindstone or a cutter by use of an appliance called rotoblator, etc., among which a preferable method is selected according to the properties of the angiostenosis portion and the conditions of the patient.

A diagnostic catheter is mainly used as an aid to observation of the angiostenosis portion or to judgment for selection of the treating means, in the percutaneous treatment of such angiostenosis portion, and is used also for observation of the conditions after treatment.

Examples of the diagnostic catheter include an ultrasound catheter for sensing by an ultrasonic detector, and an optical tomographic imaging apparatus utilizing low-interference light.

Among these diagnostic catheters, the ultrasound catheter needs to be inserted into a complicatedly bent portion such as a coronary artery of a heart; therefore, at the time of insertion, it is a common practice to preliminarily insert a guide wire to the diseased part and then advance the ultrasound catheter along the guide wire. Accordingly, the ultrasound catheter is provided at its distal end with a lumen for inserting the guide wire therein for the purpose of moving the catheter along the guide wire (this lumen is hereinafter referred to as guide wire lumen).

The guide wire lumen is generally provided only on the distal end side, in the direction of insertion into an organism, in relation to the position of the ultrasonic detector. This is because the image pickup by the ultrasonic detector is hindered if the guide wire lumen is present in the direction in which ultrasound is generated by the ultrasonic detector.

Besides, in order to minimize the range of insertion of the catheter into an organism, it is desirable that the ultrasonic detector for picking up an image of the organism is provided as close as possible to the distal end of the ultrasound catheter. Therefore, the guide wire lumen provided on the distal end side of the ultrasonic detector must be small in axial length.

Accordingly, the ultrasound catheter has had problems as follows: the operationally of the catheter is poor, and the catheter would not move along the guide wire as desired; the guide wire would be bent, to damage a blood vessel or the like, at the time of drawing away the catheter out of the body; and the catheter would be bent at the proximal end of the guide wire lumen.

The present invention has been made in consideration of the above circumstances. Accordingly, it is an object of the present invention to provide a catheter capable of being enhanced in operationally without hindering pickup of an image.

SUMMARY OF THE INVENTION

In order to attain the above object, according to the present invention, there is provided a catheter that includes an observation portion used for observation of the inside of an organism, an observation lumen in which said observation portion is disposed and which extends in the direction of insertion into said organism, a first guide wire lumen having a distal end and a proximal end, said first guide wire lumen is disposed substantially in parallel to said observation lumen and said proximal end of said first guide wire lumen is disposed on the distal end side in said insertion direction in relation to said observation portion and through which a guide wire is passed, and a second guide wire lumen having a distal end and a proximal end, said second guide wire lumen is disposed on an extension line of said first guide wire lumen and said distal end of said second guide wire lumen is disposed on the proximal end side in said insertion direction in relation to said observation portion and through which said guide wire is passed.

The catheter according to the present invention may further be characterized as follows.

The observation portion may be rotatable around an axis that is the extension direction of said observation lumen.

The observation portion may be movable in said observation lumen toward the extension direction.

The first guide wire lumen and the second guide wire lumen may be spaced from each other by a distance corresponding to the range of movement of the observation portion.

The observation portion may be an ultrasonic detector.

Thus, according to the present invention, the catheter includes the first guide wire lumen and the second guide wire lumen, so that the catheter is set along the guide wire in the vicinity of the distal end thereof, which makes it easier for a force of operating the catheter to be transmitted to the distal end of the catheter, and hence, enhances operationality of the catheter.

In addition, the first guide wire lumen is provided on the distal end side in the insertion direction in relation to the observation portion, and the second guide wire lumen is provided on the proximal end side in the insertion direction in relation to the observation portion, so that the observation of the organism by the observation portion is not hampered by the guide wire lumens, and the inside of the organism can be observed appropriately.

In the catheter according to the present invention, where the observation portion is rotatable with the extension direction of the observation lumen as an axis, a diseased part in a body cavity such as a blood vessel and a vas can be observed in a 360-degree mode.

Where the observation portion is movable in the extension direction of the observation lumen, it is possible to observe a diseased part over a wide range.

Where the first guide wire lumen and the second guide wire lumen are spaced from each other by a distance corresponding to the range of movement of the observation portion, the observation by the observation portion is not hindered by the guide wire lumens, even in the case of observing a wide range by the observation portion.

Where the observation portion is an ultrasonic detector, it is possible to form an ultrasonic tomographic image of a diseased part and to thereby observe the diseased part.

BRIEF DESCRIPTION OF THE DRAWINGS

These and other objects of the invention will be seen by reference to the description, taken in connection with the accompanying drawing, in which.

DETAILED DESCRIPTION OF THE PREFERRED EMBODIMENTS

Now, embodiments of the present invention will be described below, referring to the drawings.

Figure 1:
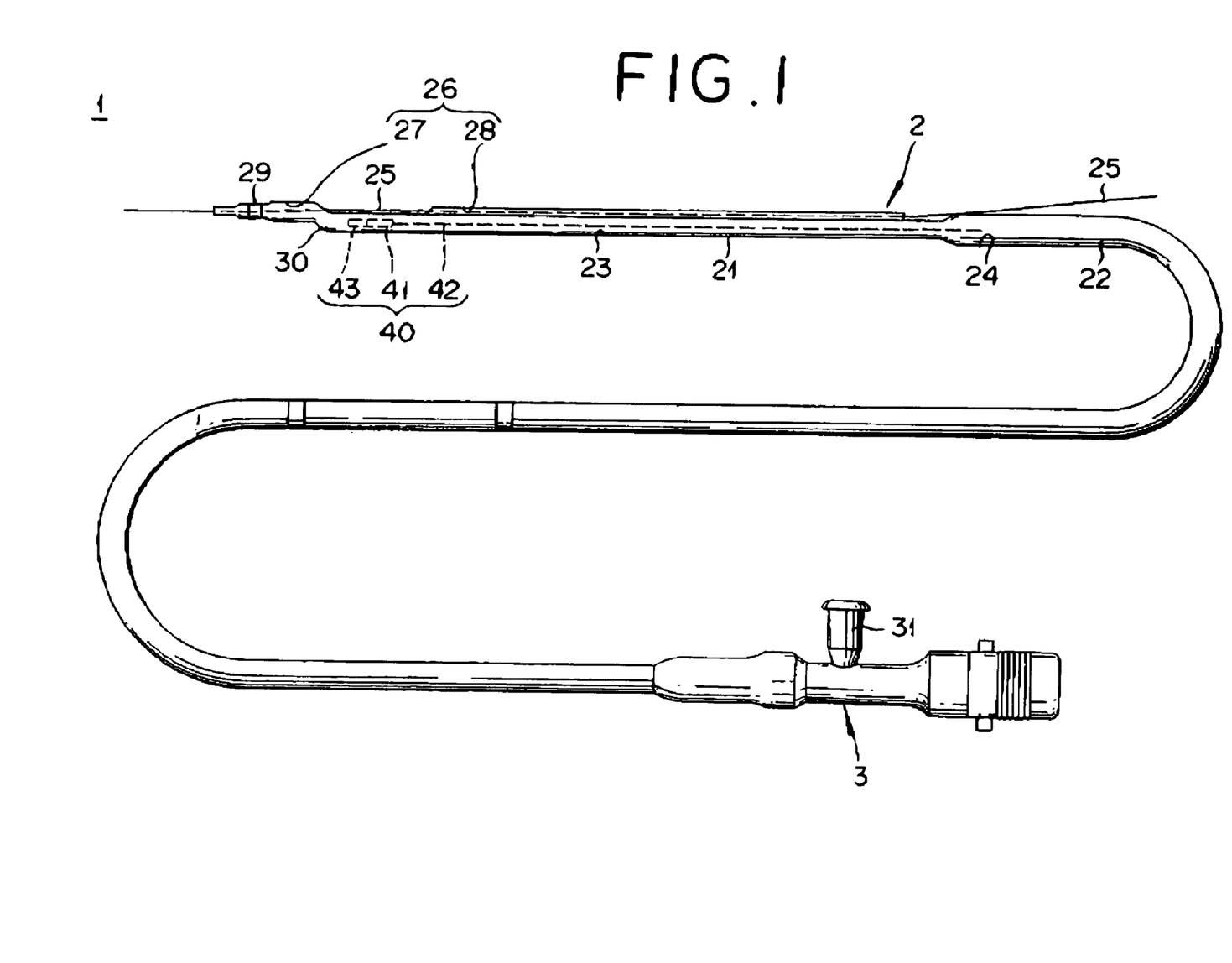
FIG. 1 shows an ultrasound catheter according to the present invention.
Figure 2:
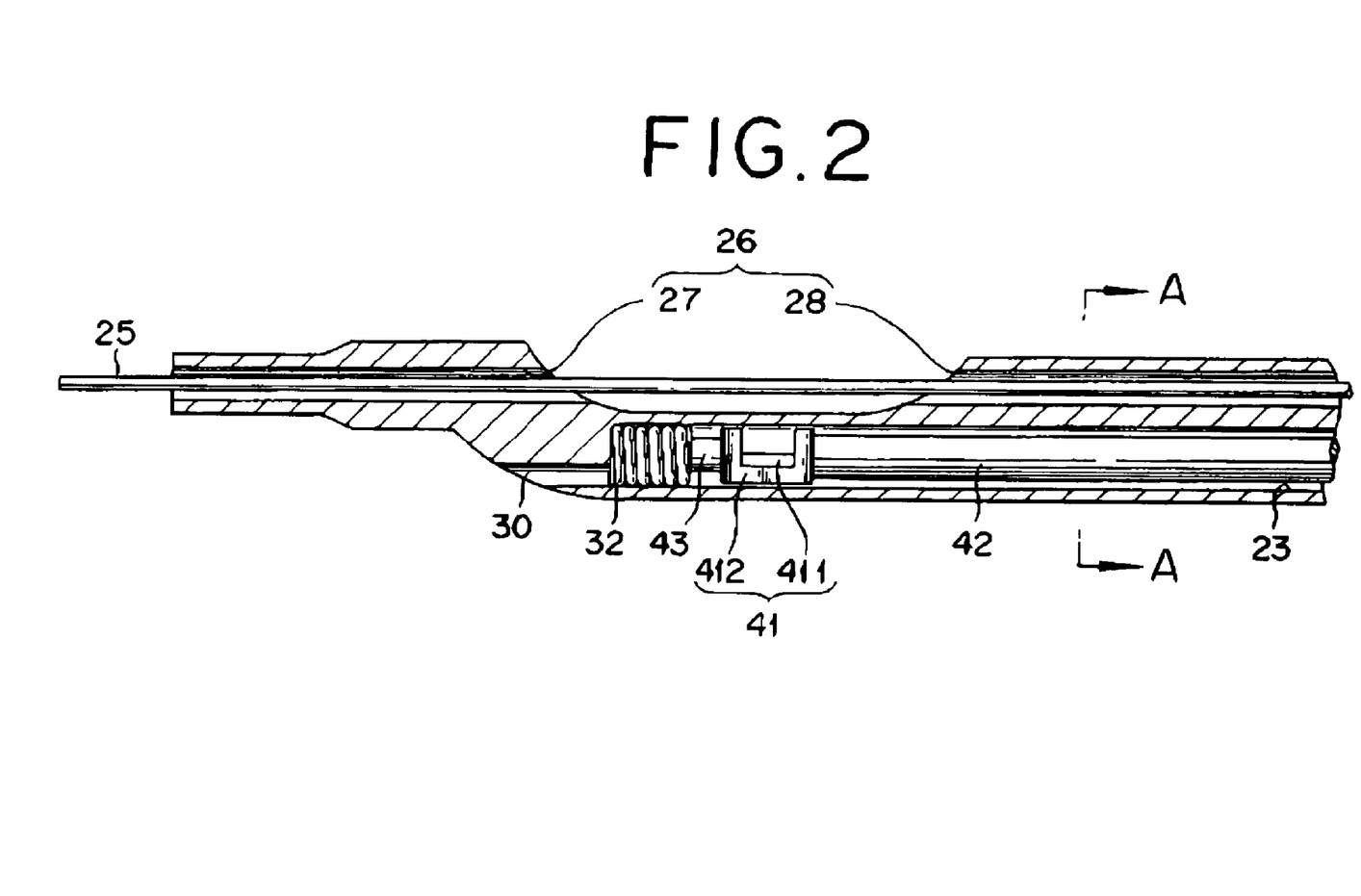
FIG. 2 is an enlarged view of a part of a distal end portion of the ultrasound catheter.

FIG. 1 shows an ultrasound catheter according to the present invention, and FIG. 2 is an enlarged view of a part of a distal end portion of the ultrasound catheter. In FIG. 2, a part is shown in dimensions different from those in FIG. 1, for illustrating the characteristic features of the present invention.

The ultrasound catheter 1 is constituted of a sheath 2, which is inserted into an organism such as a body cavity, and a hub 3, which is not inserted into the organism but is disposed on the side of the hand or fingers of the user, to be operated by the user.

The sheath 2 includes a sheath distal end portion 21, and a sheath main body portion 22. One end of the sheath main body portion 22 is joined to the sheath distal end portion 21, and the hub 3 is joined to the other end of the sheath main body portion 22.

The sheath distal end portion 21 and the sheath main body portion 22 are provided with observation lumens 23 and 24, which are in communication with each other. The observation lumens 23 and 24 are hollow passages formed in the sheath 2. The lumens 23 and 24 are formed over the range from the sheath main body portion 22 to the sheath distal end portion 21.

An imaging core 40 is disposed inside the observation lumens 23 and 24. The imaging core 40 includes a transducer unit (observation portion; ultrasonic detector) 41 for transmitting and receiving an ultrasound toward and from a tissue in a body cavity, a drive shaft 42, which is fitted with the transducer unit 41 at its distal end and which transmits a rotational force, and a rotation stabilizing coil 43 attached to the transducer unit 41.

As shown in FIG. 2, the transducer unit 41 includes an ultrasonic transducer 411 for transmitting and receiving an ultrasound, and the unit 41 also includes an ultrasonic transducer housing 412 for containing the ultrasonic transducer 411.

The ultrasonic transducer 411 generates an ultrasound toward the inside of an organism and receives an ultrasound returning after being reflected, to make it possible to form an ultrasonic tomographic image of a diseased part. The ultrasonic transducer housing 412 is formed in a recessed shape, to hold the ultrasonic transducer 411 in its recessed portion, thereby protecting the ultrasonic transducer 411.

The drive shaft 42 is flexible. Further, the shaft 42 is capable of transmitting a rotational force generated at the hub 3 to the transducer unit 41. For example, the drive shaft 42 has a fixed outside diameter and is constituted of a tubular body in the form of a multilayer coil such as a trilayer coil in which the winding direction is alternately changed in the manner of left, right, and left. The drive shaft 42 transmits the rotational force, whereby the transducer unit 41 is rotated with the extension direction of the observation lumen 23 as an axis, making it possible to observe a diseased part in a body cavity such as a blood vessel and a vas in a 360-degree mode. Besides, a signal cable for transmitting a signal detected at the transducer unit 41 to the hub 3 is passed through the inside of the drive shaft 42.

The rotation stabilizing coil 43 is attached to the distal end of the transducer unit 41 and functions as a guide for stable rotation of the transducer unit 41 when the imaging core 40 is rotated. In addition, the rotation stabilizing coil 43 can enter into a metallic coil 32 fixed to the distal end of the sheath distal end portion 21. Since the rotation stabilizing coil 43 enters into the metallic coil 32, the imaging core 40 and the sheath 2 are united with each other at the distal end of the sheath distal end portion 21, promising a structure, which is strong against bending or kink at the time of insertion of the ultra sound catheter 1 into an organism.

In addition, the observation lumens 23 and 24 not only incorporate the imaging core 40 therein but also play the role of a passage for an ultrasound transfer liquid, which is injected through a port 31 provided at the hub 3. The ultrasound transfer liquid supplied via the port 31 flows through the observation lumens 23 and 24 to the sheath distal end portion 21, i.e., it flows to fill up the portion ranging from the proximal end side to the distal end side of the sheath 21.

After the inside of the sheath 2 is filled up with the ultrasound transfer liquid, the sheath 2 is inserted into a body cavity or the like, whereby the ultrasound transfer liquid is disposed between the ultrasonic transducer 411 and the blood vessel wall, making it possible for an ultrasound to be transmitted though the ultrasound transfer liquid to a diseased part, to be reflected by the diseased part and to return from the diseased part through the ultrasound transfer liquid. Thus, the presence of the ultrasound transfer liquid makes it possible for the transducer unit 41 to pick up an ultrasonic image signal. The ultrasound transfer liquid is discharged into the organism via a discharge port 30 provided in the sheath distal end portion 21. Therefore, physiological saline or the like, which is inert to the human body, is used as the ultrasound transfer liquid.

The sheath distal end portion 21 is provided with an X-ray contrast marker 29, which ensures that the distal end position of the ultrasound catheter can be confirmed under fluoroscopy when the catheter is inserted into an organism.

The sheath distal end portion 21 is further provided with a guide wire lumen 26 as a passage for passing a guide wire 25 there through. The guide wire lumen 26 is constituted of a first guide wire lumen 27, and a second guide wire lumen 28.

The first guide wire lumen 27 is provided on the distal end side, in the direction of insertion of the ultrasound catheter 1 into an organism, and the second guide wire lumen 28 is provided on the proximal end side, namely on the side of the proximal end of the ultrasound catheter 1. In other words, the proximal end of the first guide wire lumen 27 is disposed on the distal end side of the transducer unit 41 and the distal end of the second guide wire lumen 28 is disposed on the proximal end side of the transducer unit 41. The first guide wire lumen 27 and the second guide wire lumen 28 are not connected to each other, but they are so disposed that the guide wire passages they form are substantially along the same straight line. Therefore, the guide wire 25 can pass through the guide wire lumen 26 rectilinearly without bending.

The guide wire 25 is preliminarily inserted into the vicinity of a diseased part in an organism before the insertion of the ultrasound catheter 1 into the organism to be used for guiding the ultrasound catheter 1 to the diseased part. The ultrasound catheter 1 is guided to the diseased part while fitting the guide wire lumen 26 over the guide wire 25.

Next, referring to FIG. 2, a specific structure of the neighborhood of the distal end of the sheath 2 to which the present invention is applied will be described.

As shown in FIG. 2, the guide wire lumen 26 is provided in the state of being bisected into the first guide wire lumen 27 and the second guide wire lumen 28.

The first guide wire lumen 27 is provided on the distal end side, in the direction of insertion of the ultrasound catheter 1 into an organism, in relation to the transducer unit 41 of the imaging core 40, while the second guide wire lumen 28 is provided on the proximal end side. Therefore, the guide wire lumen is absent at the outer peripheral surface of the sheath distal end portion 21, which constitutes an ultrasound passage, so that the transmission and reception of an ultra sound by the transducer unit 41 will not be prevented by the guide wire lumen 26.

Incidentally, by operating the hub 3, it is possible to move the transducer unit 41 forward (toward the distal end side) and backward (toward the proximal end side) in the observation lumen 23 via the drive shaft 42, thereby observing the inside of an organism over a wide range. In this case, if the first guide wire lumen 27 and the second guide wire lumen 28 are spaced from each other by a distance corresponding to the range of forward and backward movement of the transducer unit 41 for observation, the transmission and reception of an ultrasound will not be prevented.

Besides, the guide wire lumen 26 is provided not coaxially with the observation lumen 23 but substantially in parallel to and separately from the observation lumen 23. Therefore, since the guide wire 25 and the imaging core 40 do not pass through the same lumen, the guide wire 25 can smoothly pass through the guide wire lumen 26 without being curved.

Since the guide wire lumen 26 extends not only to the distal end portion but also to the proximal end portion of the ultrasound catheter 1, the guide wire 25 and the ultrasound catheter 1 stably cooperate with each other. At the time of inserting the sheath 2 into an organism along the guide wire 25, a force for inserting the sheath 2 is easily transmitted to the distal end in the insertion direction of the sheath 2, whereby operationality of the ultrasound catheter 1 can be enhanced.

Further, at the time of drawing away the ultrasound catheter 1 out of the organism after observation of a diseased part is finished, also, the disposition of the guide wire 25 and the sheath distal end portion 21 parallel with each other over a long distance ensures that the guide wire 25 would not be bent on the rear side of the first guide, wire lumen 27 and not injure the inside of the organism.

In addition, since the guide wire lumen 26 is constituted of the two members, namely, the first guide wire lumen 27 and the second guide wire lumen 28, even when the length of the first guide wire lumen 27 is set to be smaller than the length of the second guide wire lumen 28, the guide wire 25 can be set along the sheath 2 appropriately in the vicinity of the distal end of the sheath 2. Therefore, by reducing the length of the first guide wire lumen 27, it is possible to dispose the transducer unit 41 of the imaging core 40 close to the most distal end portion of the sheath 2, thereby promising appropriate observation of a diseased part.

Next, referring to FIGS. 3 and 4, a specific structure of the neighborhood of a joining portion between the sheath distal end portion 21 and the sheath main body portion 22 of the sheath 2 to which the present invention is applied will be described.

Figure 3:
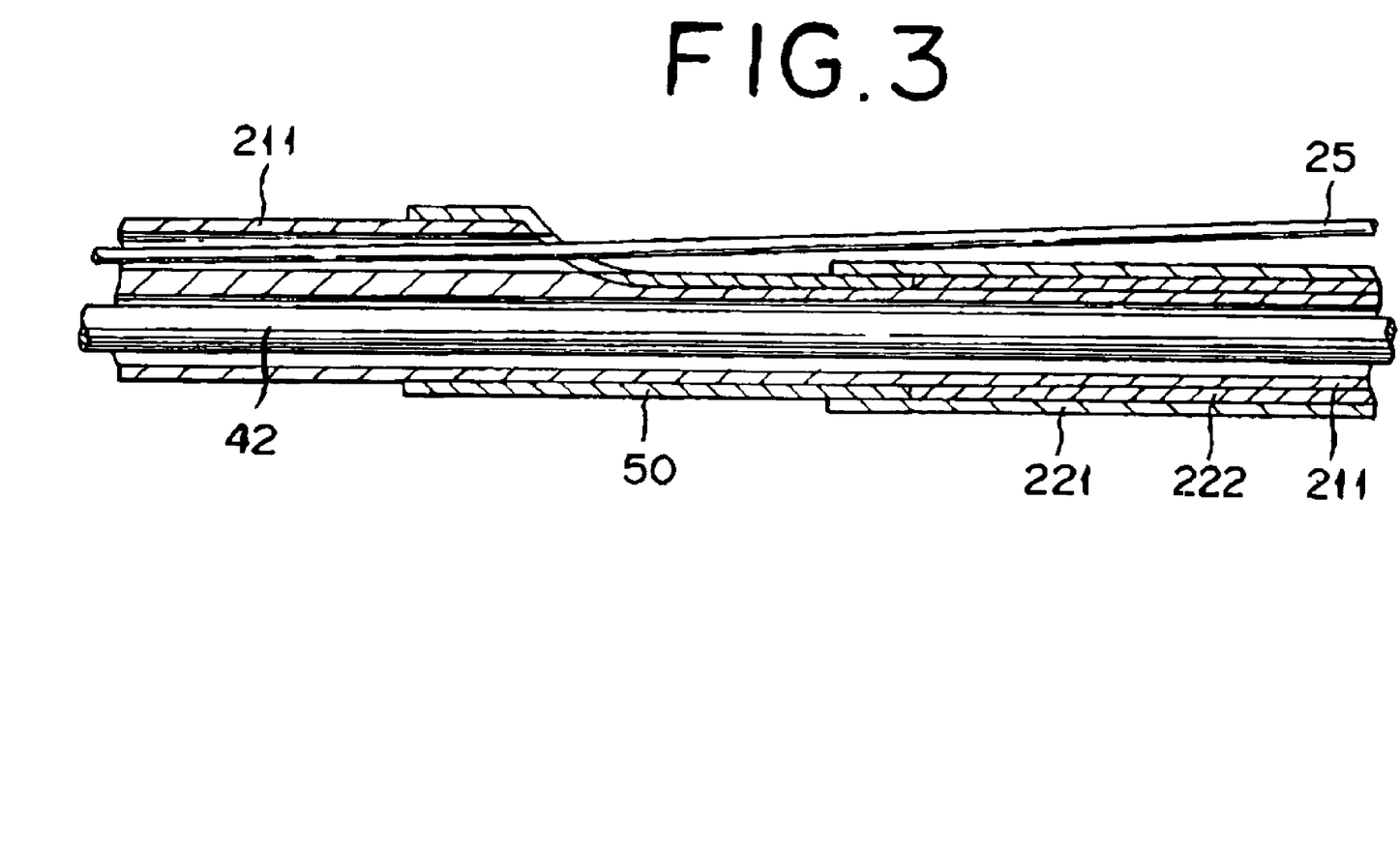
FIG. 3 shows a structure of the neighborhood of a joining portion between a sheath distal end portion and a sheath main body portion.
Figure 4:
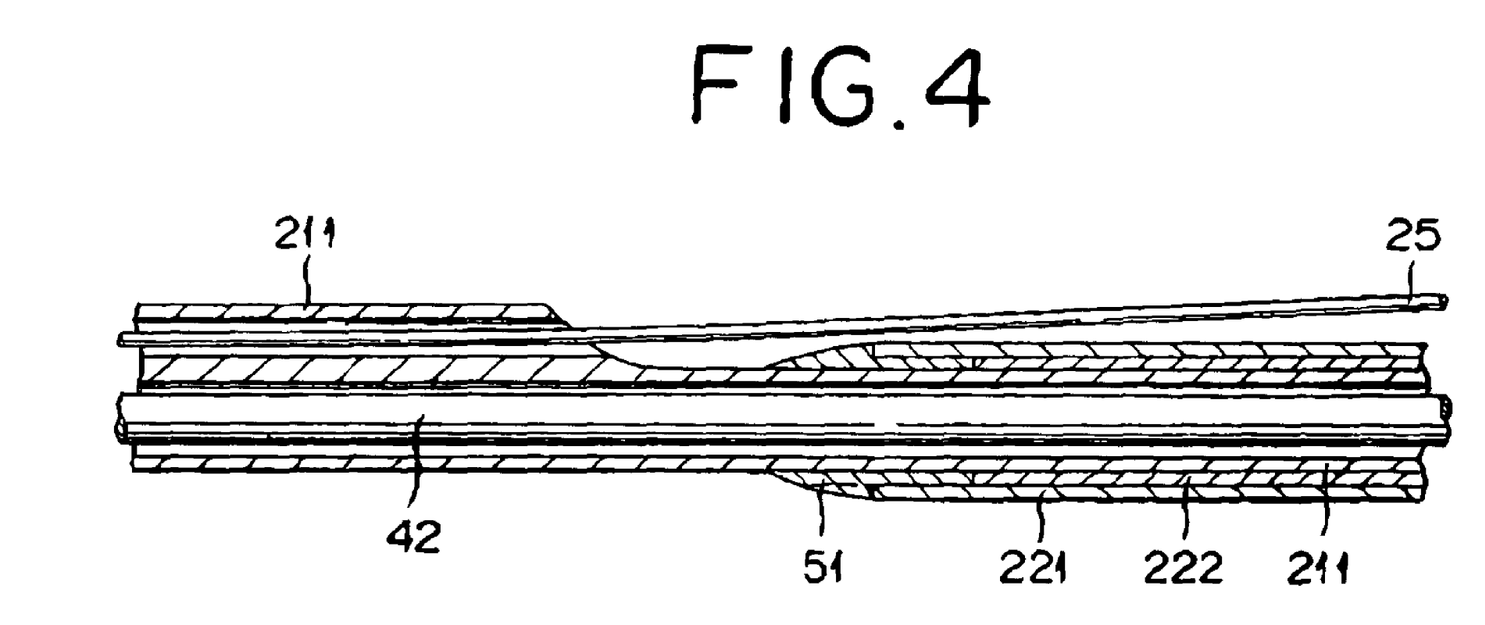
FIG. 4 shows another structure of the neighborhood of the joining portion between the sheath distal end portion and the sheath main body portion.

FIG. 3 shows a structure of the neighborhood of the joining portion between the sheath distal end portion and the sheath main body portion, and FIG. 4 shows another structure of the neighborhood of the jointing portion between the sheath distal end portion and the sheath main body portion The sheath distal end portion 21 is formed to be more flexible than the sheath main body portion 22. Therefore, the joining portion between the sheath main body portion 22 and the sheath distal end portion 21 is provided with a structure for reinforcing the difference in hardness.

A first example of the structure for this purpose is the structure shown in FIG. 3.

As shown in FIGS. 3 and 4, the sheath main body portion 22 includes a resin tube 221 as an outside wall, a metallictube 222 on the inside thereof, and a resin tube 211 further on the inside thereof, which are all fixed. The outside wall of the sheath distal end portion 21 is formed as one body with the same resin tube 211 as that extending from the sheath main body portion 22; in addition, the sheath distal end portion 21 is provided with the observation lumen 23 constituting a passage similar to the observation lumen 24 formed ranging from the sheath main body portion 22, and, further, with the guide wire lumen 26 for passing the guide wire 25 therethrough.

In the sheath main body portion 22, the tube is composed of three layers, including the metallic tube 222; therefore, the sheath main body portion 22 is harder than the sheath distal end portion 21, where the tube is composed only of the resin tube 211. Therefore, if the sheath main body portion 22 and the sheath distal end portion 21 are directly joined as they are, the difference in hardness therebetween may lead to generation of bending of kink. Of the sheath 2 at the joining portion. The bending or kink of the sheath 2 at the joining portion can be prevented, by joining the sheath distal end portion 21 and the sheath main body portion 22 to each other through a reinforcing member having an intermediate hardness between those of the sheath distal end portion 21 and the sheath main body portion 22.

The reinforcing member may be, for example, a reinforcing member 50 shown in FIG 3. The reinforcing member 50 is fitted over the resin tube 211 and is fitted inside the resin tube 221 on the distal end side in the direction of insertion of the ultrasound catheter 1 into an organism. The reinforcing member 50 is fixed to the resin tube 211 and the resin tube 221 by an adhesive or the like. Further, abuts on and is adhered to the metallic tube 222.

Another example of the reinforcing member is a reinforcing member 51 shown in FIG. 4. The reinforcing member 51 abuts on the metallic tube 222 of the sheath main body portion 22, and the resin tube 221 is fitted over the reinforcing member 51. The reinforcing member 51 is fixed to the metallic tube 222 and the resin tube 221 by an adhesive or the like.

Next, some methods for producing the sheath distal end portion 21 will be described.

FIGS. 5 to 8 are sectional views, taken along line A—A, of the sheath distal end portion shown in FIG. 2.

Figure 5:
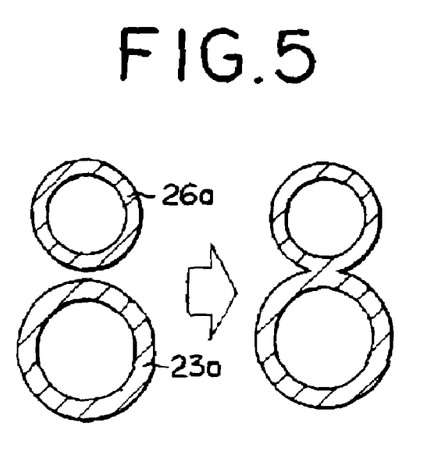
FIG. 5 is a sectional view, taken along line A—A, of the sheath distal end portion shown in FIG. 2.

In a first method of producing the sheath distal end portion 21, first, as shown on the left side in FIG. 5, a monolayer tube 26a for constituting the guide wire lumen 26 and a monolayer tube 23a for constituting the observation lumen 23 are prepared. Then, as shown on the right side in FIG. 5, parts of the outer peripheries of the monolayer tube 26a and the monolayer tube 23a are adhered to each other, whereby the guide wire lumen 26 and the observation lumen 23 substantially parallel to each other can be obtained.

Figure 6:
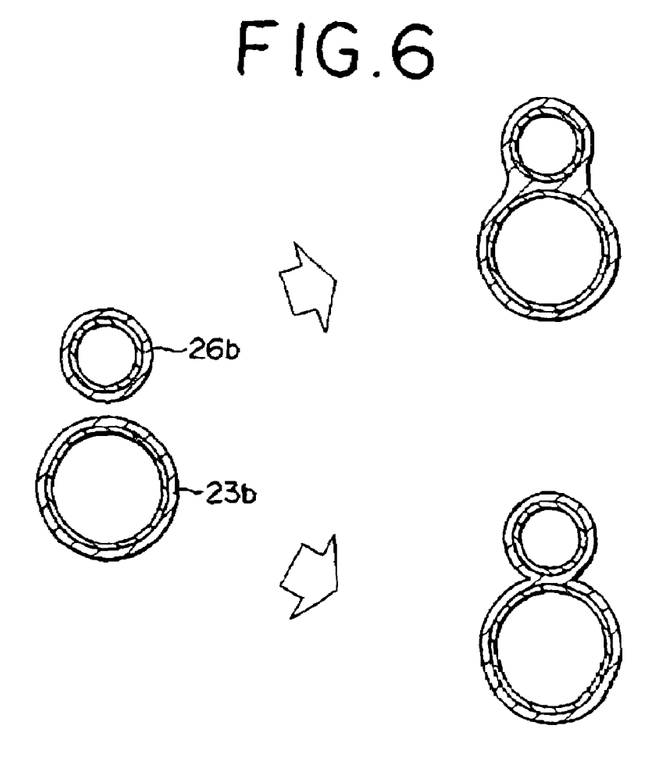
FIG. 6 is another sectional view, taken along line A—A, of the sheath distal end portion shown in FIG. 2.

Here, as shown in FIG. 6, instead of the monolayer tube 26a and the monolayer tube 23a, a multilayer tube 26b and a multilayer tube 23b may be adhered to each other. In the case of using the multilayer tubes 26b and 23b, also, in the same manner as in the case shown in FIG. 5, parts of the outer peripheries of the multilayer tubes 26b and 23b are adhered to each other, whereby the guide wire lumen 26 and the observation lumen 23 substantially parallel to each other can be obtained.

Figure 7:
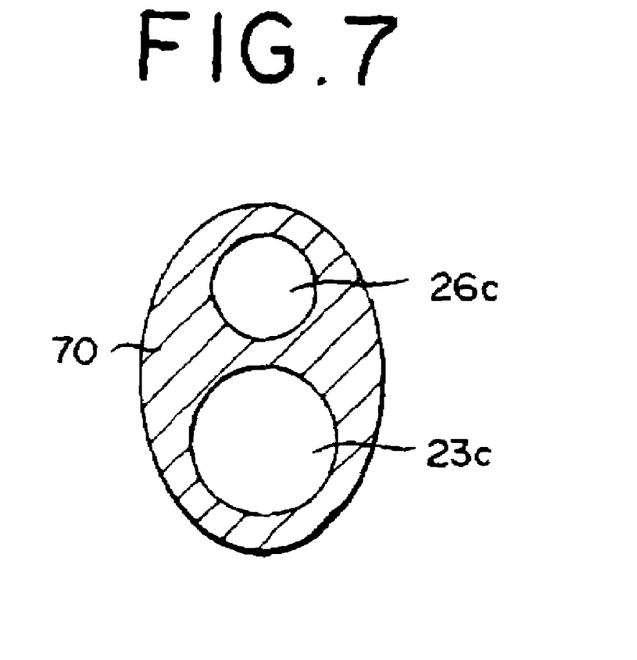
FIG. 7 is a further sectional view, taken along line A—A, of the sheath distal end portion shown in FIG. 2.

In a second method of producing the sheath distal end portion 21, as shown in FIG. 7, a tube 70 having a diametral size sufficient for forming the guide wire lumen 26 and the observation lumen 23 therein is prepared. Then, substantially parallel passages 26c and 23c are formed in the tube 70, whereby the guide wire lumen 26 and the observation lumen 23 are made to be substantially parallel to each other.

Figure 8:
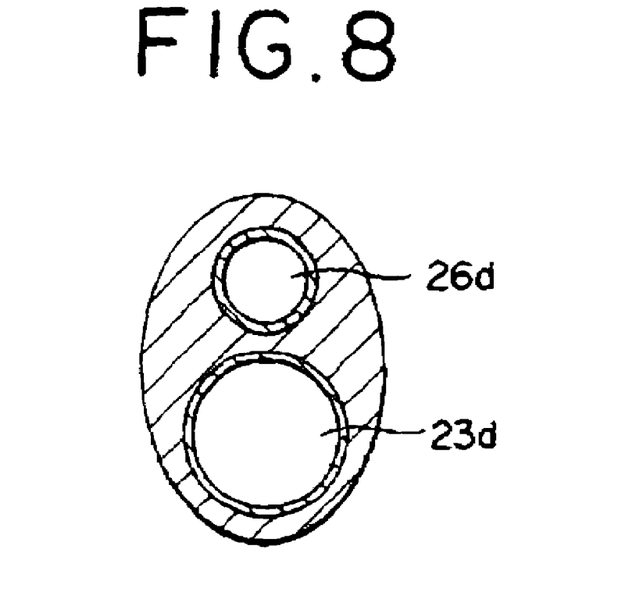
FIG. 8 is a still another sectional view, taken along line A—A, of the sheath distal end portion shown in FIG. 2.

Here, as shown in FIG. 8, by forming two substantially parallel passages in the tube 70 and fitting multilayer tubes 26d and 23d in the passages, also, it is possible to provide the sheath distal end portion 21 with the guide wire lumen 26 and the observation lumen 23 substantially parallel to each other.

Since the sheath distal end portion 21 is thus formed so that the guide wire lumen 26 and the observation lumen 23 are substantially parallel to each other, the guide wire 25 and the imaging core 40 will not pass coaxially, so that the guide wire 25 can be smoothly slidden without bending.

As described above, according to the present invention, the guide wire lumen 26 is divided into the first guide wire lumen 27 and the second guide wire lumen 28, and the second guide wire lumen 28 is disposed on the distal end side in relation to the transducer unit 41 of the imaging core 40. Therefore, as compared with the conventional design in which the guide wire lumen is provided only on the distal end side of the transducer unit 41, the guide wire 25 is set along the distal end of the sheath 2 over a longer distance, so that an operating force exerted at the hub 3 can be easily transmitted to the distal end of the ultrasound catheter 1, and operationality of the ultrasound catheter 1 can be enhanced.

According to the present invention, in addition, the guide wire lumen 26 is bisected into the portion on the distal end side and the portion on the proximal end side in relation to the transducer unit 41 so that the guide wire lumen 26 is absent in the direction in which an ultrasound is generated from the transducer unit 41 toward the inside of an organism. Therefore, the transmission and reception of the ultra sound by the transducer unit 41 will not be hampered by the guide wire lumen 26, and it is possible to achieve appropriate observation of the inside of the organism.

While the case of applying the present invention to an ultrasound catheter has been described in the above embodiments, the invention can also be applied to other diagnostic catheters. For example, the present invention is applicable to a diagnostic catheter utilizing Optical Coherence Tomography (OCT). In the OCT, a measuring light beam is made to be incident on an organism, and the organism can be observed based on the light returning after undergoing scattering, absorption, reflection, or refraction in the organism.

While preferred embodiments of the invention have been described using specific terms, such description is for illustrative purposes only, and it is to be understood that changes and variations may be made without departing from the spirit or scope of the following claims.

The entire disclosure of Japanese Patent Application No, 2002-260193 filed of Sep. 5, 2002 including specification, claims, drawings, and summary is incorporated herein by reference in its entirety.

The invention claimed is:

1. A catheter comprising:
an observation portion used for observation of the inside of an organism,
a sheath comprising an observation lumen in which said observation portion is disposed and which extends in the direction of insertion into said organism,
a first guide wire lumen having a distal end and a proximal end, said first guide wire lumen is disposed substantially in parallel to said observation lumen and said proximal end of said first guide wire lumen is disposed on the distal end side in said insertion direction in relation to said observation portion and through which a guide wire is passed,
a second guide wire lumen having a distal end and a proximal end, said second guide wire lumen is disposed on an extension line of said first guide wire lumen and said distal end of said second guide wire lumen is disposed on the proximal end side in said insertion direction in relation to said observation portion and through which said guide wire is passed;
said first guide wire lumen and said second guide wire lumen both being disposed on the sheath;
the proximal end and the distal end of the first guide wire lumen each possessing an opening, and the proximal end and the distal end of the second guide wire lumen each possessing an opening, the opening at the proximal end of the first guide wire lumen and the opening at the distal end of the second guide wire lumen being spaced apart from one another such that when a guide wire is positioned in both the first guide wire lumen and the second guide wire lumen a portion of the guide wire is located exterior of the sheath; and
the proximal end of the first guide wire lumen and the distal end of the second guide wire lumen being positioned relative to one another to permit a guide wire extending between the proximal end of the first guide wire lumen and the distal end of the second guide wire lumen to extend exterior of the sheath in a straight line without bending.

2. The catheter as set forth in claim 1, wherein said observation portion is rotatable around an axis which is the extension direction of said observation lumen.

3. The catheter as set forth in claim 2, wherein said observation portion is movable in said observation lumen toward the extension direction.

4. The catheter as set forth in claim 2, wherein said observation portion is an ultrasonic detector.

5. The catheter as set forth in claim 1, wherein said observation portion is movable in said observation lumen toward the extension direction.

6. The catheter as set forth in claim 5, wherein said observation portion is an ultrasonic detector.

7. The catheter as set forth in claim 5, wherein said first guide wire lumen and said second guide wire lumen are spaced from each other by a distance corresponding to the range of movement of said observation portion.

8. The catheter as set forth in claim 7, wherein said observation portion is an ultrasonic detector.

9. The catheter as set forth in claim 1, wherein said observation portion is an ultrasonic detector.

10. The catheter as set forth in claim 1, wherein the opening at the proximal end of the first guide wire lumen is positioned on a distal side of the observation part and the opening at the distal end of the second guide wire lumen is positioned on a proximal side of the observation part.

* * * * *